(12) United States Patent
Cox et al.

(10) Patent No.: US 7,812,009 B2
(45) Date of Patent: Oct. 12, 2010

(54) MASTITIS TREATMENT

(75) Inventors: Peter Gerardus Franciscus Cox, Bouchemaine (FR); Joseph Antonius Clemens Maria Lohuis, Afferden (NL); Selma Marianne Hensen, Mook (NL)

(73) Assignee: Intervet International B.V., Boxmeer (NL)

( * ) Notice: Subject to any disclaimer, the term of this patent is extended or adjusted under 35 U.S.C. 154(b) by 477 days.

(21) Appl. No.: 10/539,672

(22) PCT Filed: Dec. 10, 2003

(86) PCT No.: PCT/EP03/14051

§ 371 (c)(1),
(2), (4) Date: Jun. 14, 2005

(87) PCT Pub. No.: WO2004/054538

PCT Pub. Date: Jul. 1, 2004

(65) Prior Publication Data

US 2006/0058273 A1  Mar. 16, 2006

(30) Foreign Application Priority Data

Dec. 16, 2002  (EP) .................................. 02080265

(51) Int. Cl.
  *A01N 45/00* (2006.01)
  *A61K 31/56* (2006.01)
  *A61K 31/545* (2006.01)
  *C07J 5/00* (2006.01)
(52) U.S. Cl. ..................... 514/171; 514/200; 552/576
(58) Field of Classification Search ................. 514/171, 514/200; 552/576
  See application file for complete search history.

(56) References Cited

U.S. PATENT DOCUMENTS 4,112,073 A  9/1978  Ono

FOREIGN PATENT DOCUMENTS

EP  1 585 497 B1  3/2008

OTHER PUBLICATIONS

Lohuis, J.A.C.M. et al: "Effect of Steroidal Anti-Inflammatory Drugs on *Escherichia coli* . . ." J. of Dairy Science, (Jan. 1989) Amer. Dairy Science Assoc. V72, N1, p. 241-249.
Farnsworth, R.J. et al: "The Effect of Penicillin, Dihydrostreptomycin and Prednisolone Treatment . . ." Canadian J. of Comparative Medicine-Revue, (Jul. 1975) V39, N3 p. 340-348.
Faull, W.B. et al: "Treatment of clinical mastitis: Two intramammary formulations compared" Veterinary Record, British Veterinary Assoc.(Feb. 8, 1975) V96, N6 p. 127-129.
Hornish, R.E. et al: Cephalosporins in Veterinary Medicine-Ceftiofur Use in Food . . . (Jul. 2002) Current Topics in Medicinal Chemistry, Bentham Sci. Pub. V2, N7,p. 717-731, NL.
Breitschwerdt et al., Prednisolone at Anti-Inflammatory or Immunosuppressive Dosages in Conjunction with Doxycycline Does Not Potentiate the Severity of *Rickettsia rickettsii* infections in Dogs, Antimicrobial Agents and Chemotherapy, Jan. 1997, pp. 141-147, vol. 41, No. 1.
Geleta et al., Excretion of [$^3$H]prednisolone in clinically normal and experimentally infected bovine udders, Am. J. Vet. Res., Aug. 1984, vol. 45, No. 8.
Orden et al., In Vitro Activities of Cephalosporins and Quinolones against *Escherichia coli* Strains Isolated from Diarrheic Dairy Calves, Antimicrobial Agents and Chemotherapy, Mar. 1999, pp. 510-513, vol. 43, No. 3.
Shpigel et al., Efficacy of Cefquinome for Treatment of Cows with Mastitis Experimentally Induced Using *Escherichia coli*, J. Dairy Sci., pp. 318-325, vol. 80.
Matsuda et al., Abstract, Combination Chemotherapy for Klebsiella Mastitis, Journal of Veterinary Medicine, Japan, 1995, pp. 985-988, vol. 48, No. 12.
Summary of Product Characteristics of Product CEPHAGUARD LC, marketing authorization of 2001.
Report on prednisolone issued by the Committee for veterinary medicinal products, EMEA/MRL/629/99-FINAL, published in Jul. 1999.
Notice of Opposition in French and Notice of Opposition in English for European patent No. 1 585 497 B1.
Opposition response dated Jul. 30, 2009.

*Primary Examiner*—Sreeni Padmanabhan
*Assistant Examiner*—Samira Jean-Louis
(74) *Attorney, Agent, or Firm*—Allen C. Turner; David M. Gryte

(57) ABSTRACT

A pharmaceutical composition for intramammary administration to a nonhuman mammal comprising an antibacterial agent and prednisolone, wherein the composition comprises at least 20 mg of prednisolone, and its use for the treatment of clinical mastitis.

10 Claims, 6 Drawing Sheets

EFFECT OF PREDNISOLONE AT DIFFERENT DOSAGES ON MEAN UDDER SCORES OF COWS WITH ENDOTOXIN MASTITIS
ARROWS INDICATE TIME OF TREATMENT

EFFECT OF INTRAMAMMARY TREATMENT ON RECTAL TEMPERATURE OF COWS WITH STREPTOCOCCUS UBERIS MASTITIS. ARROWS INDICATE TIME OF TREATMENT

NUMBER OF LEUKOCYTES IN BLOOD FROM COWS WITH ENDOTOXIN-INDUCED MASTITIS BEFORE, DURING AND AFTER TREATMENT WITH CEPHAPIRIN (300 MG) AND PREDNISOLONE (20 MG).

BACTERIOLOGICAL AND CLINICAL CURE RATE AFTER I.M.M. TREATMENT WITH COMP B (AMOXICILLIN+ CLAVULANIC ACID + 10 MG PREDNISOLONE) AND COMP. A (CEPHAPIRIN +20 MG PREDNISOLONE)

MASTITIS TREATMENT

RELATED APPLICATIONS

This application is related to PCT/EP2003/014051 filed Dec. 10, 2003, which claims priority to EP Application 02080265.8 filed Dec. 16, 2002.

The present invention relates to a pharmaceutical composition for intramammary administration to a non-human mammal comprising an antibacterial agent and prednisolone and its use for the treatment of clinical mastitis.

Mastitis is one of the major problems of agricultural milk production because it causes morbidity, loss of milk production and culling of dairy cows, sheep or goats. Despite preventive care by selective breeding, milking technology and hygiene measures, it is often impossible to prevent infections, most of which are caused by bacterial pathogens.

Clinical mastitis may be expressed by the production of abnormal milk (flakes, clots or watery secretions) with the infected udder showing clinical signs (swelling, heat, pain on palpation). In cases of acute clinical mastitis, these signs may be combined with general signs (fever, anorexia, depressed general condition).

It is the main objective of therapy of clinical mastitis to diminish the local and systemic signs of disease or to shorten the period with disease symptoms, to minimise losses in milk production, to obtain a bacteriological cure of the infected quarter of the udder and to keep the withdrawal periods for meat and milk short. Antibiotic treatment is the principle method for eliminating existing infections. Unfortunately a true bacteriological cure, whereby all infecting micro-organisms are eliminated from the affected quarter, occurs not always for most bacterial species. The cure rate of a mastitis treatment is dependent on the treatment itself, how long the infection has been present, age of the cow and the type of micro-organism involved.

Corticosteroids, such as e.g. prednisolone have been incorporated in several antibiotic preparations to treat mastitis during lactation.

In treatment of clinical mastitis corticosteroids aid in reducing swelling and pain and enhance the removal of toxic secretions as well as promote better diffusion of intramammary infusions.

The general effects of corticosteroids are numerous and widespread, they include: metabolic effects (e.g. gluconeogenesis, proteolysis, lipolysis), hormonal effects (e.g. suppression of endogeneous cortisol production), effects on electrolyte and water balance (mineralocorticoideffect), a negative effect on cell division and DNA synthesis in various cells (e.g. lymphocytes, fibroblasts, mucosal cells), haematologic effects (leucocytosis characterised by neutrophilia and lymphopenia), anti-inflammatory effects and effects on the immune system.

These effects are generally depending on the type of corticosteroid, the dosage, the formulation and the administration route.

A particular undesired effect of corticosteroids in most of the indications is the suppressive effect on the host immune system. Corticosteroids are known to decrease some humoral and cellular responses of the host immune system, for instance by decreasing lymphocyte responses to mitogens, decreasing the synthesis of endogeneous mediators and lowering the number of circulating lymphocytes. These effects are considered to be dosage depending (see e.g. The Merck Veterinary Manual, Eighth Edition, 2002, Chapter steroids).

The use of prednisolone is considered as being efficacious in the treatment of clinical mastitis after intramammary administration, but up to now only low dosages of an equivalent of 10 mg/unit dose of prednisolone were used in practice because of the known disadvantages, particular in terms of immune suppression.

The antiinflammatory effects of prednisolone in clinical mastitis after intramammary administration of a low dosage of maximum of 10 mg/unit dose with or without antibacterial agents have been described e.g. by Bywater et al in: Proceedings of 15$^{th}$ World Bulatrics congress, (1988, Palma de Mallorca), Lees et al, Flem. Vet. J., Vol 62 (suppl. 1), pp 43-54, 1991 and Lohuis et al, J Dairy Sci, Vol 72, pp 241-249, 1989.

Corticosteroids have been incorporated in several antibacterial products that are commercialised for treatment of mastitis during lactation. Examples are Synolux LC™ (Pfizer) with the antibacterials amoxicillin trihydrate, clavulanic acid and 10 mg of prednisolone; Mastijet Forte™ (Intervet) with the antibacterials neomycin, bacitracin, tetracycline and 10 mg of prednisolone; Lincocin Forte™ (Pharmacia & Upjohn) with the antibacterials lincomycin, neomycin and 5 mg of methylprednisolone.

In the commercial product Tetra Delta™ (Pharmacia & Upjohn) the antibacterials procaine penicillin, novobiocin, polymyxine B, dihydrostreptomycin, chlorobutanolanhydricum are combined with 32.5 mg of hydrocortisone. This dosage of hydrocortisone is equivalent to 13 mg of prednisolone.

Hydrocortisone has however a more pronounced mineralocorticoid effect than prednisolone. Compounds with a profound mineralocorticoid effect are less suitable for use as anti-inflammatory agent.

Lohuis et al, J Dairy Science, Vol. 72, pp 241-249, 1989 describes the improved effects of intramammary infusion of 40 mg/unit dose of prednisolone on local and systemic inflammatory signs in non-bacterial E. coli endotoxin induced clinical mastitis under experimental conditions.

The known immune suppressive side effects prevented up to now the inclusion of higher dosage of prednisolone, especially in products for the treatment of bacterial induced mastitis. In such bacterial induced mastitis cases the impact of immune suppression is more important, as the infectious agent is still virulent and a depressed defence mechanism could support the bacterial growth and therefore promote the disease.

It is therefore the object of the current invention to provide a pharmaceutical composition for the treatment of clinical mastitis for intramammary administration that displays an improved antiinflammatory effect without the drawback of immunosuppression.

The current invention provides a pharmaceutical composition for intramammary administration to a non-human mammal, comprising an antibacterial agent, prednisolone and a pharmaceutically acceptable carrier, that comprises at least 20 mg of prednisolone/unit dose.

It has been found that a composition according to the invention provides in the treatment of clinical mastitis an improved antiinflammatory efficacy on local and systemic inflammation symptoms as shown in examples 2 and 3 without the expected immunosuppressive side effects (see examples 4 and 5). Example 4 shows that the composition according to the invention does not have an influence on the white blood and milk cells, as an indicator of the main defence mechanism of the host and udder during inflammation in acute clinical mastitis. Example 5 shows that under field conditions a composition according to the invention did not show a negative effect on the bacteriological cure rate and clinical cure rate compared to treatment with a commonly used lower dosage of prednisolone.

The compound Prednisolone (11β)-11,17,21-trihydroxypregna-1,4-diene-3,20-dione ($\Delta^1$-dehydro-hydrocortisone) is a synthetic corticosteroid derived from hydrocortisone. Prednisolone is a commonly used corticosteroid in intramammary formulations. The term 'prednisolone' when used herein includes also pharmaceutically acceptable salts and esters thereof.

According to the present invention a unit dosage of the pharmaceutical composition comprises at least 20 mg of prednisolone. A typical pharmaceutical composition according to the invention comprises 20 to 40 mg of prednisolone/unit dose as defined above. Preferably the pharmaceutical composition comprises 20 to 30 mg of prednisolone/unit dose, even more preferred 20 mg of prednisolone/unit dose.

The antibacterial agent that is included in the composition can be in general an antibacterial with sufficient broad spectrum antibacterial efficacy in order to treat the most important micro-organisms causing mastitis. Such antibacterial agents are generally known in the art.

Preferred is a β-lactam antibiotic, e.g. a penicillin or cephalosporin. In a preferred embodiment it is a cephalosporin. Cephalosporins are semisynthetic antibiotics derived from cephalosporin C, a natural antibiotic produced by the mould *Cephalosporium acremonium*. Cephalosporins belong to the class of β-lactam antibiotics and are classified as first- (e.g. cephapirin, cephalothin, cephaloridine, cefazolin), second- (cefamandole, cefuroxime, cefoxitin), third- (e.g. cefotaxime, ceftriaxone, cefoperazone) or fourth-generation (cefepime, cefpirome, cefquinome) products according to the order of their introduction and the position and type of sidechain that has been incorporated into the basic molecule. At present cephalosporins are widely used for the treatment of infections. The term "cephalosporins" when used herein includes pharmaceutically acceptable salts and esters thereof.

A particular preferred cephalosporin compound is cephapirin. Cephapirin (3-[(acetoxy)methyl]-8-oxo-7[[4-pyridinylthio)acetyl]amino]-5-thia-1-azabicyclo-[4.2.0]oct-2-ene-2-carboxylic acid) is a cephalosporin of the first generation. Preferably the pharmaceutically acceptable salt of cephapirin is the sodium salt.

In another preferred embodiment of the invention the fourth-generation cephalosporin cefquinome (INN—international non-proprietary name) is used. Cefquinome is a semisynthetic aminothiazolyl cephalosporin resembling cefotaxime, but with a bicyclic pyridinium group at the C-3 position (Isert et al, Seibert et al, $29^{th}$ Interscience Conference on Antimicrobial Agents and Chemotherapy Houston, Tex., 1989). Preferably the pharmaceutically acceptable salt of cefquinome is the sulphate salt.

A typical pharmaceutical composition according to the invention comprises 10 to 500 mg of the antibacterial agent/unit dose depending on the potency of the compound. Preferably the pharmaceutical composition comprises 200 to 400 mg of cephapirin/unit dose, more preferred 300 mg.

Alternatively the pharmaceutical composition comprises 50 to 150 mg of cefquinome/unit dose, more preferred 50 to 100 mg.

The pharmaceutically acceptable carrier for the active ingredients (the antibacterial agent and prednisolone) is selected so as to be non-toxic, veterinary acceptable, compatible with the active ingredients, and of a viscosity to permit administration, whilst controlling the release characteristics of the drug particles.

In accordance with common practice, the pharmaceutical composition according to the invention for intramammary administration comprises a suspension or solution of the active ingredient in a suitable vehicle, which can be made of an aqueous or oily base.

Oils that can be used for the oily base in pharmaceutical compositions are in general natural, e.g. vegetable, semisynthetic or synthetic mono-, di- or tri glyceride. Vegetable oils that can be used are e.g. sesame oil, olive oil, cottonseed oil, castor oil, arachis oil, or coconut oil.

The pharmaceutically acceptable carrier in the composition according to the invention preferably comprises an oily base and optionally comprises one or more additives such as thickening agents, desiccants and antioxidants. Suitable pharmaceutical excipients are known in the art. Such pharmaceutical excipients for the carrier for intramammary formulations are e.g. described in "Gennaro, Remington: The Science and Practice of Pharmacy" (20th Edition, 2000), incorporated by reference herein.

Conventional thickening agents are e.g. aluminium stearate, silica, or fatty acid esters such as glycerol monostearate. A suitable amount of a thickening agent is within the range of 2 to 30% by weight. Desiccants are e.g. silicates, activated clay, silica gel, and molecular sieve. Especially preferred is sodium aluminium silicate. A suitable amount of a desiccant that can be used is within the range of 5 to 15% by weight, preferably 5-10%. Suitable antioxidants are e.g. butylhydroxytoluene or hydroxyanisole. The antioxidant will usually be present within the range of 0.01 to 10% by weight. Other additives may also be present in the oily vehicle in minor proportions.

The current invention further provides a process for preparing a pharmaceutical composition according to the invention comprising the steps of mixing an oil and optionally additives and suspending the antibacterial agent and the prednisolone in the carrier.

DETAILED DESCRIPTION OF THE PREFERRED EMBODIMENTS

Figure 1:
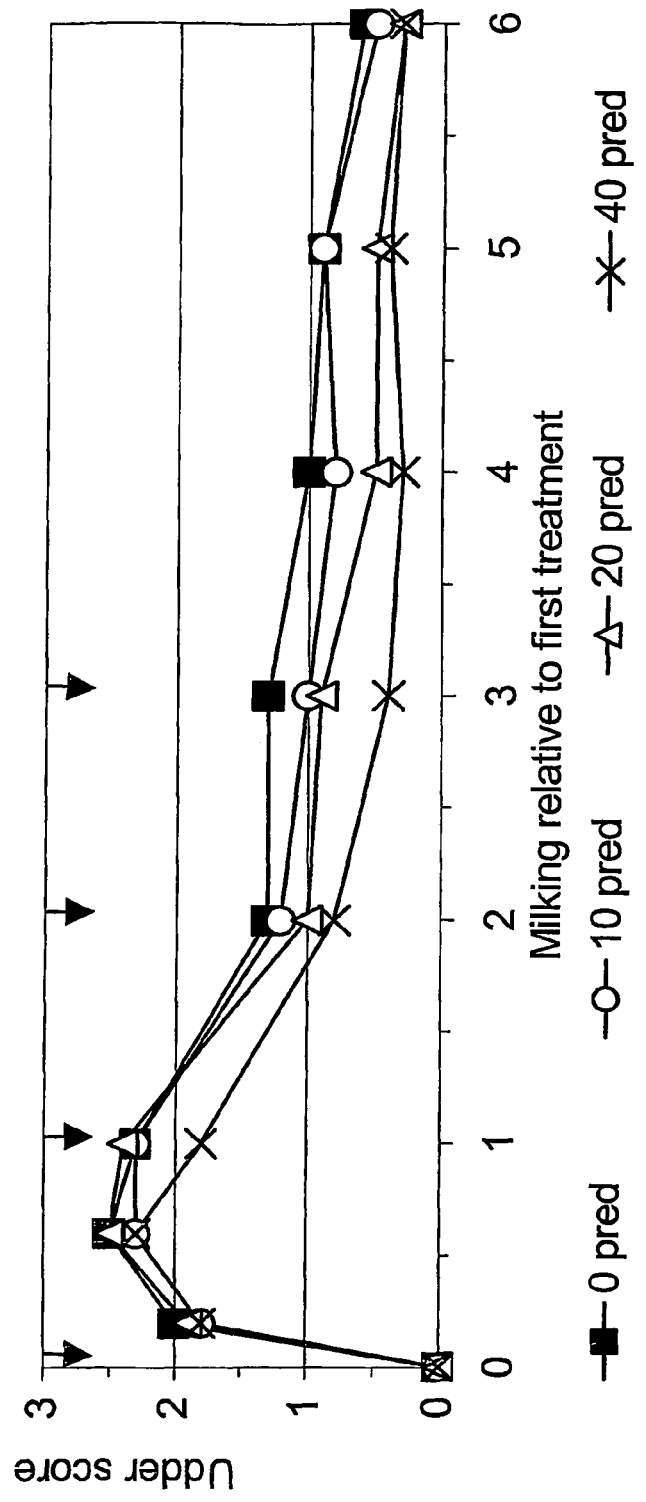
FIG. 1 is a graph depicting the effect of prednisolone at different dosages on mean udder scores of cows with endotoxin-induced mastitis.

More specifically the current invention provides a process according to the invention in which the carrier is formed by mixing at an appropriate temperature the oil and the additives, in order to form a gel. After cooling down this carrier, the antibacterial agent and the prednisolone are added to it at room temperature using a suitable mixing device in order to obtain a homogeneous dispersion. The mixture is then filled into the unit dose tubes or syringes.

A single unit dose is the content of an applicator e.g. a syringe or tube that will be administered intramammary through the teat canal into the mammary gland of a lactating animal. A single unit dose of the composition will normally contain 1 to 20 grams preferably 2 to 10 grams of the formulated pharmaceutical composition. Typical unit doses may contain 6-8 grams of the formulated pharmaceutical composition.

The chosen formulation may be filled into the tube or syringe packs of the conventional type for intramammary administration. Such an intramammary syringe is provided with a cannula nozzle for insertion into the teat to allow extrusion directly into the mammary gland via the teat canal.

Furthermore the current invention provides the use of an antibacterial agent and prednisolone for the manufacture of a medicament comprising at least 20 mg of prednisolone/unit dose for the treatment of mastitis in non-human mammals.

In the treatment of clinical mastitis the content of one intramammary injector (unit dose) of the composition according to the invention is repeatedly administered after milking to the infected quarter of the udder until the disease symptoms cease (normally the treatment duration is 1-10 days).

The invention provides furthermore the use of prednisolone for the manufacture of a medicament comprising at least 20 mg of prednisolone/unit dose for the treatment of bacterial induced clinical mastitis in non-human mammals.

In the composition for the treatment of bacterial induced clinical mastitis additionally an antibacterial agent as described above might be present.

The pharmaceutical composition according to the invention can be applied principally to all non-human mammalian species that need treatment of clinical mastitis such as e.g. cattle, camel, buffalo, goat, or sheep. Mastitis may affect any species, but is especially important in ruminants that are used for milk production for human consumption such as cattle, buffalo, sheep and goat.

EXAMPLE 1

Manufacturing of the Composition

For a 20 kg batch in a production vessel (Fryma VME-20 with wall scraper, dissolver and internal colloid mill) 17.9 kg of arachis oil, 4 g BHT and 1.2 kg of glycerol monostearate are mixed. 0.1% water is added and the mixture is heated at 121° C. for 1 hour. The added water is removed by further heating at 121° C. for 30 minutes under nitrogen. The mixture is cooled to 25° C. and 803.0 g of cephapirin sodium and 50.4 g of prednisolone are added under mixing. The mixture is colloided for 30 minutes at ambient temperature (below 30° C.). The suspension is filled into the intramammary injectors.

EXAMPLE 2

Effect of Different Dose of Prednisolone on Signs of Local Inflammation

Materials and Methods

Twenty-four cows were allotted to four groups of 6 cows each, according to milk production and parity. All cows were intramammary infused into two homo-lateral quarters with 100 μg Escherichia coli endotoxin (purified lipopolysacchide (LPS) obtained from E. coli 0111:B4) in 20 ml saline.

The test preparations contained cephapirin and prednisolone in an oily carrier. Four different dose levels of prednisolone were tested: 0 mg (group 1), 10 mg (group 2), 20 mg (group 3) and 40 mg (group 4) per injector (8 g) together with 200 mg of cephapirin sodium.

Cows were treated with the contents of one injector per endotoxin infused quarter when the first signs of clinical mastitis were evident, i.e. 1.5 hours after endotoxin infusion. The next three treatments were infused immediately after consecutive afternoon or morning milkings (12 hours interval) during 2 days. In total four treatments were administered.

Udder scores: The condition and swelling of quarters were determined by palpation once daily after morning milking from day−7 to day−1 relative to endotoxin infusion and twice daily after milkings from day+1 to day+6 relative to endotoxin infusion. The day of endotoxin infusion, swelling of quarters was assessed by palpation approximately every half hour during ±12.5 hours after infusion. The scoring system provides scores 0 to 4. Higher values refer to increased and more severe signs of local inflammation.

Results:

The average udder scores are presented in FIG. 1.

A clear dose effect relation was observed for prednisolone and the sum of the udder scores; higher dosages of prednisolone resulted in lower sum of udder scores. Sum of udder scores treated with 40 mg prednisolone was significantly lower from 8 hours post infusion up to the evening milking of day 5 compared to the udder scores of placebo quarters (0 mg prednisolone) and of quarters treated with 10 mg prednisolone. Quarters treated with 20 mg prednisolone had a lower sum of udder scores than the placebo quarters during the same period.

EXAMPLE 3

Rectal Temperature (Systemic Sign of Inflammation in Mastitis) in Cows with Experimental Streptococcus uberis Mastitis after Intramammary Administration of Cephapirin Sodium Alone Compared to the Administration of Cephapirin Sodium +20 mg Prednisolone Together and Non-Treatment Material and Methods:

Eighteen lactating cows were intramammarily inoculated into the two left quarters with Streptococcus uberis (±1000 CFU/quarter). At 2 days after challenge, when all cows had clinical signs of mastitis (i.e. quarter foremilk modification and/or udder swelling), cows were allotted to three groups of six cows each, to produce groups with similar parity and milk production.

One group was treated with cephapirin alone (group 1), one group was treated with cephapirin and 20 mg prednisolone (group 2) and one group was non-treated (group 3). Cows included in group 1 and group 2 were treated in the 2 left inoculated quarters at day 2 after challenge. The first treatment was applied after a morning milking, and the following three infusions were performed immediately after the next 3 consecutive milkings. Cows of group 3 were left untreated. However, due to the occurrence of too severe clinical signs of mastitis, three cows from the untreated control group had to be treated for ethical reasons at 2 and half days after challenge. These 3 cows were treated intramammarily with cephapirin sodium and 20 mg prednisolone. The content of one injector was administered into each challenged quarter at four consecutive milkings. These 3 cows were excluded from the control group. The rectal temperature was determined from day 9 before first treatment up to day 19 after first treatment.

Figure 2:
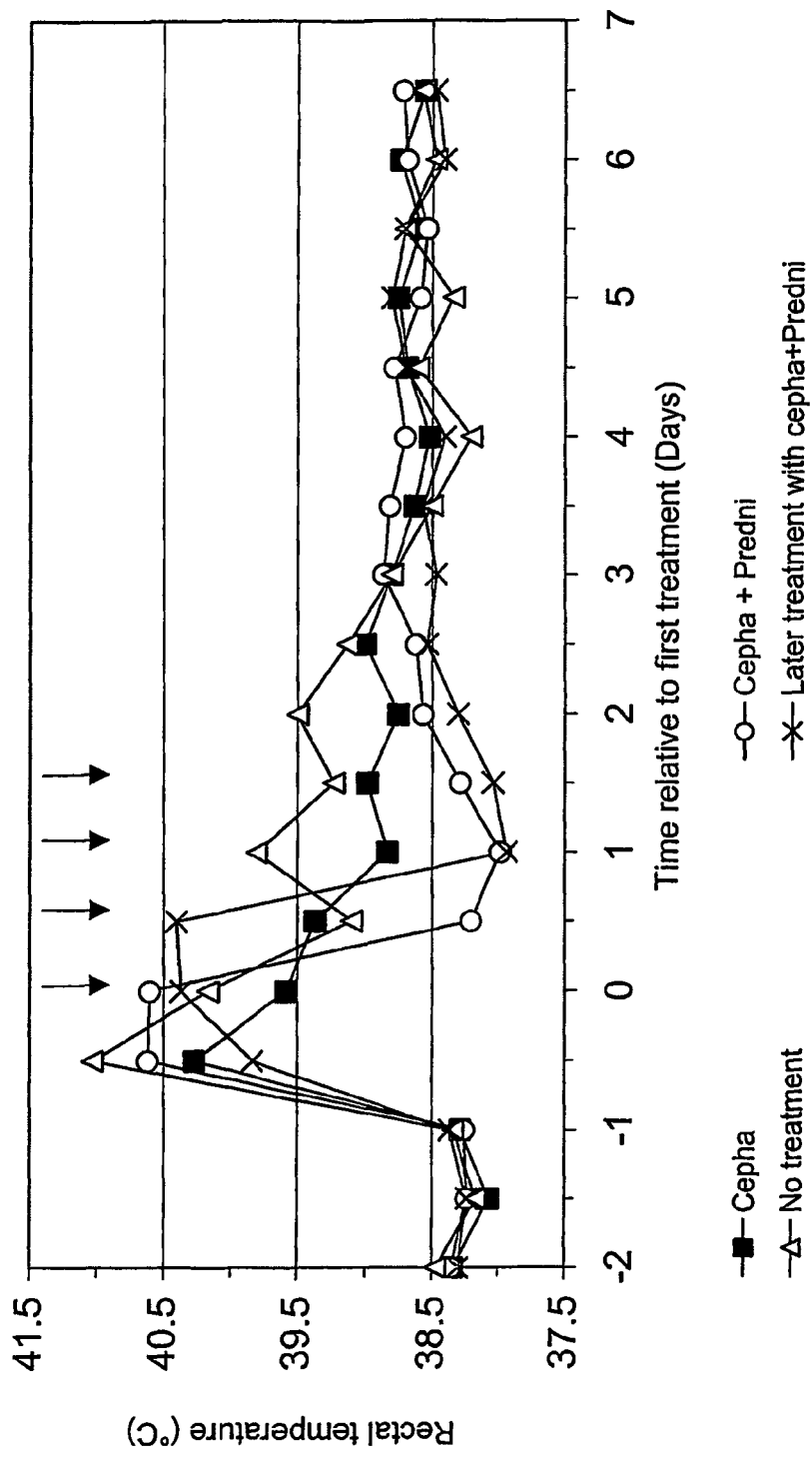
FIG. 2 is a graph depicting the effect of intramammary treatment on rectal temperatures with S. uberis mastitis.

Results:

Rectal temperatures are presented in FIG. 2.

Rectal temperatures observed at day 0 (evening) and day 1 (morning after first treatment in the group treated with cephapirin and 20 mg prednisolone were significantly lower than rectal temperatures observed in other groups. After treatment with cephapirin alone the average rectal temperature decreased slowly. Average rectal temperature of the untreated cows was >39° C. until day 2 (evening). Average rectal temperature of the 3 cows treated later with cephapirin +20 mg prednisolone was reset to normal temperature (<39° C.) at the next milking following the first treatment.

EXAMPLE 4

Effect on Intrammammary Administration of Prednisolone on Polymorphonuclear Leucocytes (PMN) Functions Isolated from Blood and Milk of Cows with Experimental *E. coli* Endotoxin Induced Mastitis Materials and Methods Fifteen cows were allotted to three groups of 5 cows each, according to milk production and parity. Cows were intramammary infused into 2 homo-lateral quarters with 100 μg *Escherichia coli* endotoxin (purified lipopolysacchide (LPS) obtained from *E. coli* 0111:B4) in 20 ml saline.

Cows were treated with the contents of one injector per endotoxin infused quarter when the first signs of clinical mastitis were evident, i.e. approximately 2 hours after endotoxin infusion. One group was treated with 300 mg of cephapirin, one group with 300 mg of cephapirin and 20 mg of prednisolone and one group was the non-treated control. The test preparations contained cephapirin and prednisolone in an oil carrier.

The next three treatments were infused immediately after consecutive afternoon or morning milkings (12 hours interval) during 2 days.

Blood samples were collected from the jugular vein at 24 hours before endotoxin infusion and 1.5, 8, 48 and 72 hours after endotoxin infusion.

Quarter milk from the endotoxin infused quarters was collected 24 h before infusion, 1.5 h after infusion (i.e. 0.5 h before first treatment) and 8 h, 48 h, and 72 h after endotoxin infusion.

Figure 3:
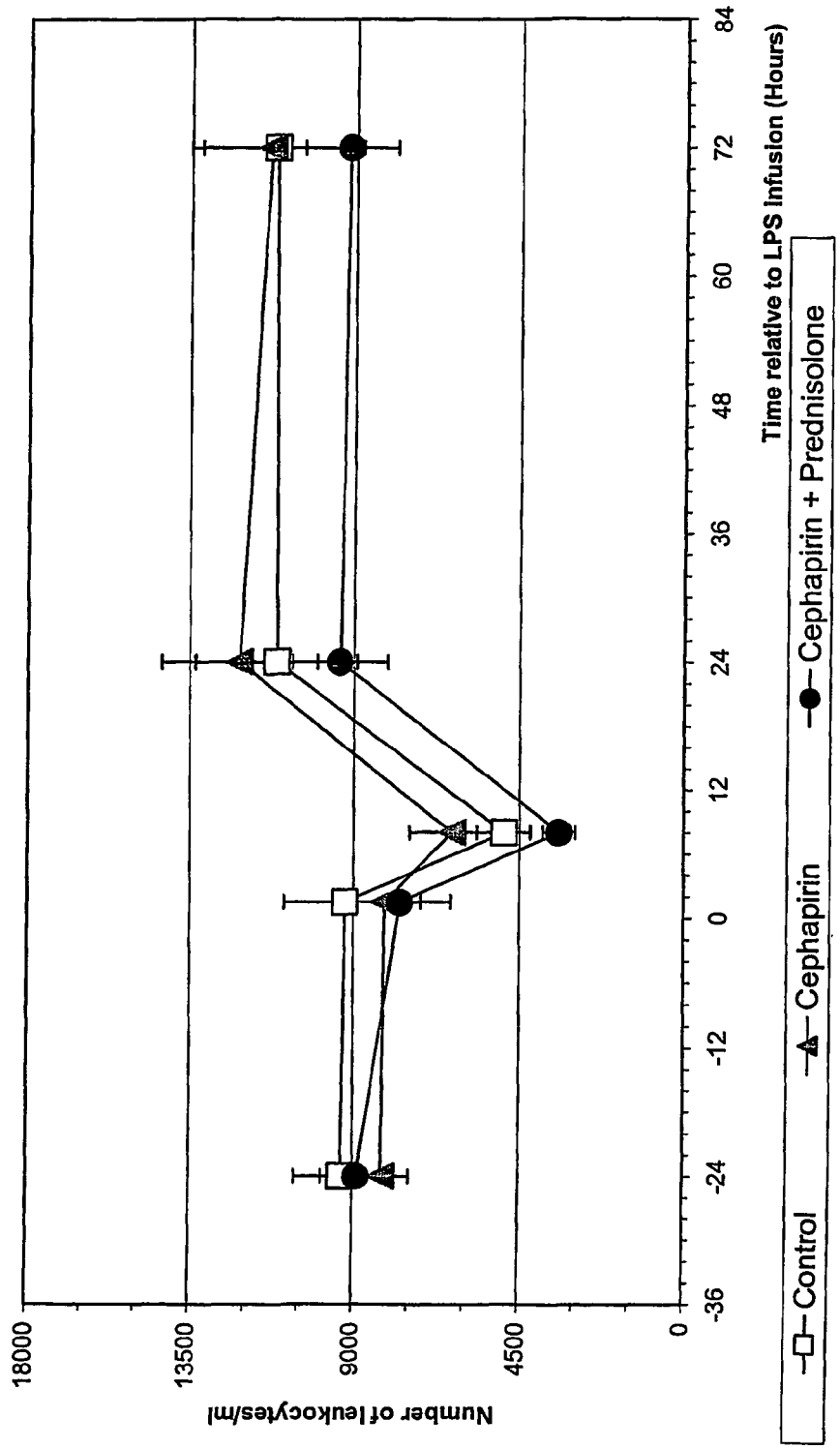
FIG. 3 is a graph depicting the number of leukocytes in blood from cows with, endotoxin-induced mastitis before, during and after treatment with cephapirin (300 mg) and prednisolone (20 mg).

Results:

Effect on blood PMN: At 8 h after endotoxin infusion, total leukocyte counts in blood is lower in cows treated with cephapirin and prednisolone (group 3) than in cows treated with cephapirin alone, but not different from total leukocyte counts in blood from not treated cows (Table 1 and FIG. 3). The decrease of circulating leukocytes is the result of leukopenia induced by the LPS that is a normal phenomenon involved in the process of immune defense. In case of a negative effect of prednisolone this leukopenia would be suppressed resulting in a lower decrease in the count of circulating leukocytes.

TABLE 1

Effect of prednisolone on number of leukocytes in blood from cows with endotoxin-induced mastitis.

| Treatment | | Number of leukocytes in blood at time relative to endotoxin infusion (Hours) | | | | |
|---|---|---|---|---|---|---|
| | | −24 | 1.5 | 8 | 24 | 72 |
| Control (no treatment) | Mean | 9336 | 9229 | 4910 | 11126 | 11167 |
| | Std | 2835 | 3760 | 1636 | 4946 | 5236 |
| Cephapirin | Mean | 8217 | 8157 | 6329 | 12148 | 11317 |
| | Std | 1677 | 2218 | 2573 | 4744 | 4245 |

TABLE 1-continued

Effect of prednisolone on number of leukocytes in blood from cows with endotoxin-induced mastitis.

| Treatment | | Number of leukocytes in blood at time relative to endotoxin infusion (Hours) | | | | |
|---|---|---|---|---|---|---|
| | | −24 | 1.5 | 8 | 24 | 72 |
| Cephapirin + Prednisolone | Mean | 8895 | 7734 | 3399 | 9391 | 9153 |
| | Std | 2201 | 3093 | 986 | 2919 | 2855 |

[a] Treatments with cephapirin alone or cephapirin and prednisolone were applied at 2, 8, 24 and 36 hours after endotoxin infusion.

No difference on maturity, size, granularity, phagocytosis and oxidative burst of blood PMNs was observed between group 3 and groups 1 and 2. During their maturation process, the size of the PMN decreases whereas granularity increases. Oxidative burst is an indicator of PMN activity. If prednisolone had a negative effect on PMN, size of PMN would be increased, granularity would be decreased and/or oxidative burst would be reduced. However, it was not observed after intramammary infusion of the 20 mg of prednisolone.

Figure 4:
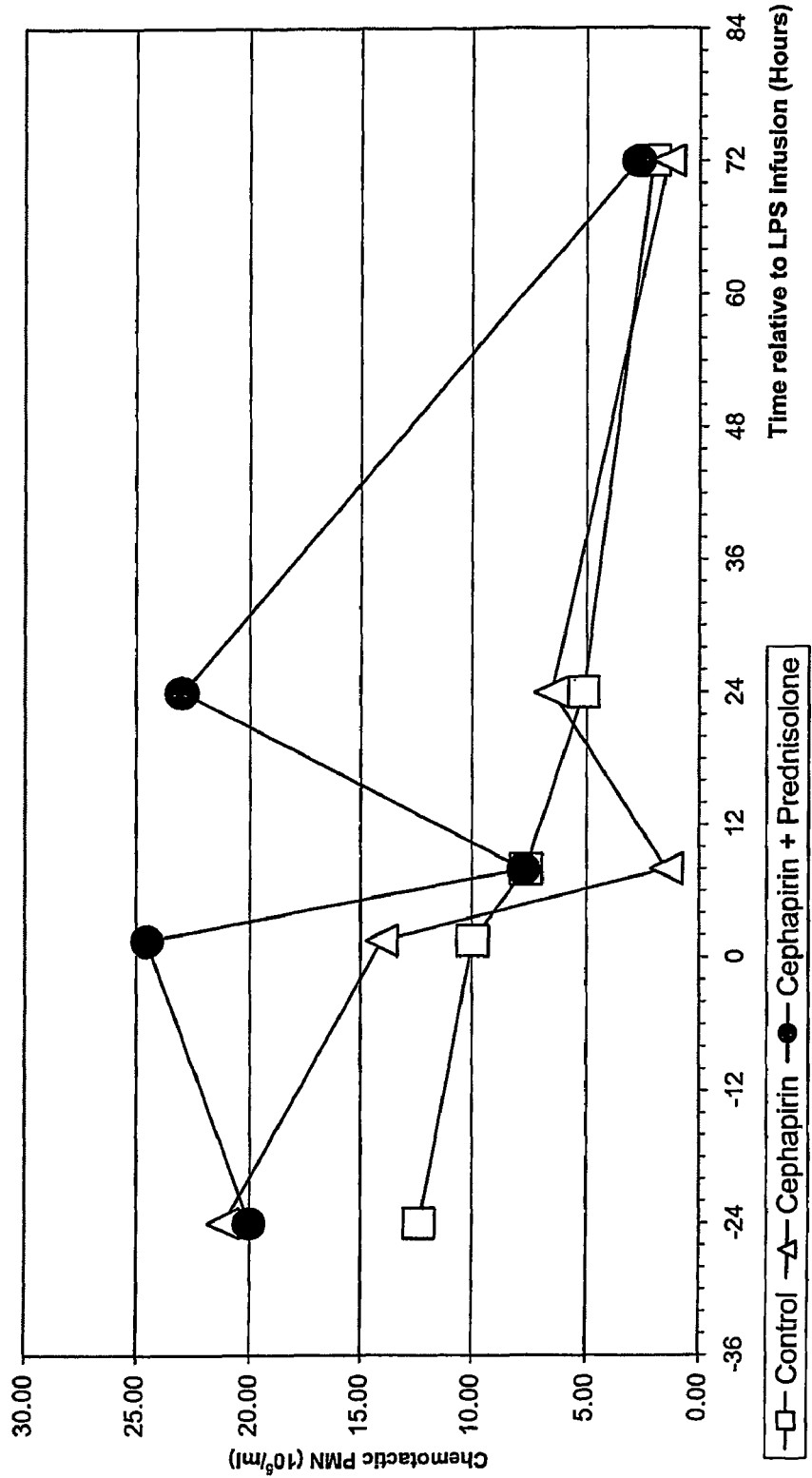
FIG. 4 is a graph depicting PMN chemotaxis from cows with endotoxin-induced mastitis before, during and after, treatment with cephapirin (300 mg) and prednisolone (20 mg).

At 24 h after endotoxin infusion the chemotaxis of blood PMNs was higher in group 3 than in group 1 or 2. (Table 2 and FIG. 4). 20 mg prednisolone seems to increase the ability of PMN to migrate into the udder since chemotaxis of blood PMNs increases after intramammary infusion of cephaprin and 20 mg of prednisolone.

TABLE 2

Effect of prednisolone on chemotaxis of leukocytes in blood from cows with endotoxin-induced mastitis.

| Treatment[a] | | Chemotactic PMN (×10⁵/ml) at time relative to endotoxin infusion (Hours) | | | | |
|---|---|---|---|---|---|---|
| | | −24 | 1.5 | 8 | 24 | 72 |
| Control (no treatment) | Mean | 12.37 | 9.96 | 7.60 | 5.11 | 2.02 |
| | Std | 6.55 | 6.05 | 9.31 | 5.85 | 1.28 |
| Cephapirin | Mean | 21.15 | 14.04 | 1.42 | 6.50 | 1.35 |
| | Std | 11.68 | 4.11 | 1.53 | 6.40 | 0.85 |
| Cephapirin + Prednisolone | Mean | 20.01 | 24.49 | 7.70 | 22.96 | 2.65 |
| | Std | 26.80 | 28.71 | 9.04 | 13.09 | 1.50 |

[a]Treatments with cephapirin alone or cephapirin and prednisolone were applied at 2, 8, 24 and 36 hours after endotoxin infusion.

Figure 5:
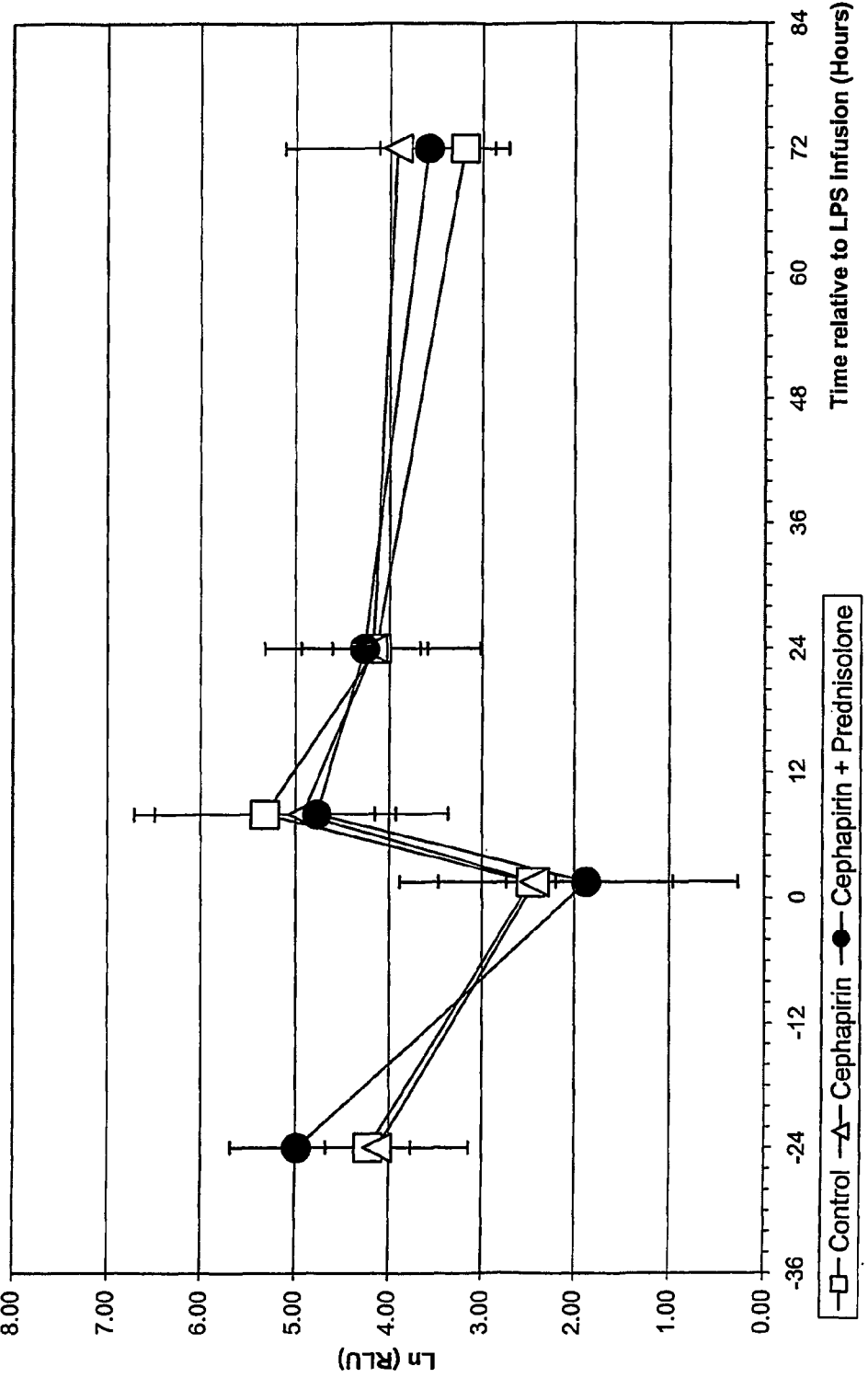
FIG. 5 is a graph depicting chemiluminescence in quarters infused with LPS: comparison between control group and groups treated with cephapirin (300 mg) and prednisolone (20 mg).

Effect on milk PMN: No difference was observed for chemiluminiscence of PMNs isolated from milk between groups 1, 2 and 3 as it is shown in FIG. 5. Chemiluminescence is an indicator of PMN activity, based on measurement of light photons generated by reactive oxygen compounds issued from PMN activity. Chemiluminescence is strongly related to oxydative burst. In case of a negative impact on the defence mechanism a greater drop in the chemiluminescence would have been observed.

Conclusions

The higher dosage of prednisolone (20 mg) did not affect blood and milk PMN morphology and functions.

EXAMPLE 5

Efficacy of a Composition with 20 mg Prednisolone and an Antibacterial Compound Compared to a Composition with 10 mg of Prednisolone Under Field Conditions Material and Methods:

Lactating cows with clinical mastitis in a single quarter (571) were treated intramammarily either with a composition A (n=260) comprising 300 mg cefapirin sodium and 20 mg of prednisolone four times with a 12 h interval or with composition B (n=254) comprising 200 mg amoxicilline, 50 mg clavulanic acid and 10 mg of prednisolone three times with a 12 h interval. These administration schedules correspond to the recommended dosage of the products. The efficacy of the treatment was determined by the bacteriological cure rate (elimination of pathogen identified on day 0) at day 14, and day 21 and the clinical cure rate (affected quarter produces normal milk and no signs of clinical mastitis anymore) at days 14 and 21.

Results:

Bacteriological cure: A cow was considered as bacteriologically cured when, both on Days 14 and 21, the milk sample from the affected quarter was free from pathogen(s) present at day 0 (at admission prior to treatment). For clinical mastitis, treatment were considered as a failure for which cows were not yet clinically cured on the first post-treatment sampling (Day 14). These cows had to be excluded from the second sampling (Day 21) Therefore, these cows were considered as being not bacteriologically cured (definition according to guidelines for the conduct of efficacy studies for intramammary products for use in cattle EMEA/CVMP/344/99).

Clinical cure: A cow was considered clinically cured when, at the time of the first post-treatment sampling, day 14 the cow produced normal milk and showed no signs of clinical masttis in the affected quarter cured (definition according to guidelines EMEA/CVMP/344/99).

Figure 6:
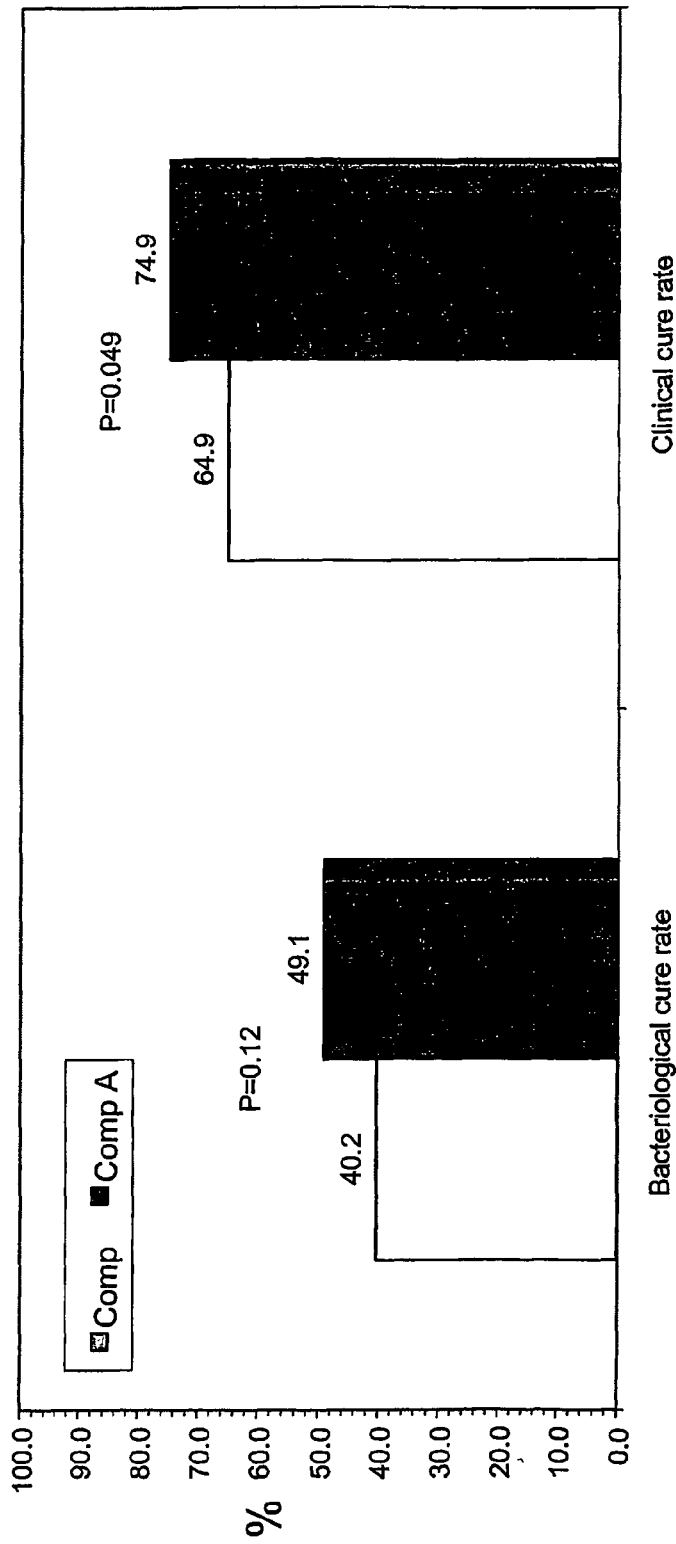
FIG. 6 is two bar graphs depicting the bacteriological and clinical cure rate after I.M.M. treatment with Comp B (amoxicillin and clavulanic acid+10 mg prednisolone) and Comp. A (cephapirin+prednisolone (20 mg).

The parameters for efficacy are the outcome variables "bacteriological cure" (cure/non-cure) and "clinical cure" (cure/non-cure). The results in Table 3 and FIG. 6 are expressed as numbers and percentages of cows cured.

wherein the pharmaceutical composition comprises 20-40 mg of prednisolone per unit dose; and further wherein the increased anti-inflammatory efficacy while not increasing immunosuppressive side effects may be determined by displaying a similar leukocyte count upon administration to the non-human mammal when administered intramammarily, as compared to the non-human mammal to whom the pharmaceutical composition has not been thus administered.

2. The pharmaceutical composition according to claim 1, wherein the composition comprises prednisolone in an amount of 20 to 30 mg per unit dose.

3. The pharmaceutical composition according to claim 1, wherein the cephalosporin is cephapirin.

4. The pharmaceutical composition according to claim 1, wherein the cephalosporin is cefquinome.

5. The pharmaceutical composition according to claim 1, wherein the cephalosporin is present in an amount of 10 to 500 mg per unit dose.

6. A process for preparing the pharmaceutical composition according to claim 1, comprising the steps of mixing an oil and one or more pharmaceutically acceptable additives to form a carrier, and suspending the cephalosporin and the prednisolone in the carrier.

7. A pharmaceutical composition for intramammary administration to a non-human mammal, the pharmaceutical composition providing increased anti-inflammatory efficacy while not increasing immunosuppressive side effects in the non-human mammal, wherein:
the pharmaceutical composition comprises:
a cephalosporin;
20 mg prednisolone per unit dose; and
a pharmaceutically acceptable carrier;

TABLE 3

Overall bacteriological and clinical cure rate (numbers and percentage) by treatment and country

| | Bacteriological cure | | | | | | Clinical cure | | | | | |
|---|---|---|---|---|---|---|---|---|---|---|---|---|
| | Composition B | | | Composition A | | | Composition B | | | Composition A | | |
| Country | no. cases | no. cured | % cured | no. cases | no. cured | % cured | no. cases | no. cured | % cured | no. cases | no. cured | % cured |
| NL | 56 | 21 | 37.5 | 50 | 21 | 42.0 | 60 | 37 | 61.7 | 51 | 33 | 64.7 |
| Hu | 39 | 19 | 48.7 | 45 | 20 | 44.4 | 43 | 32 | 74.4 | 49 | 37 | 75.5 |
| Fr | 31 | 15 | 48.4 | 24 | 19 | 79.2 | 34 | 21 | 61.8 | 28 | 26 | 92.9 |
| UK | 53 | 17 | 32.1 | 50 | 23 | 46.0 | 54 | 34 | 63.0 | 51 | 38 | 74.5 |
| Total | 179 | 72 | 40.2 | 169 | 83 | 49.1 | 191 | 124 | 64.9 | 179 | 134 | 74.9 |
| | Chi-square Adj. Contin. P = 0.12 | | | | | | Chi-square Adj. Contin. P = 0.049 | | | | | |

Conclusion

The higher dosage of prednisolone (20 mg) did not negatively influence the bacteriological cure rate.

The invention claimed is:

1. A pharmaceutical composition for intramammary administration to a non-human mammal, said pharmaceutical composition providing increased anti-inflammatory efficacy in the non-human mammal while not increasing immunosuppressive side effects in the non-human mammal to which it has been administered, wherein:
the pharmaceutical composition comprises:
a cephalosporin,
prednisolone, and
a pharmaceutically acceptable carrier;

wherein the increased anti-inflammatory efficacy while not increasing immunosuppressive side effects may be determined by an increased chemotaxis of blood leukocytes upon administration to the non-human mammal when administered intramammarily, as compared to the non-human mammal to whom the pharmaceutical composition has not been thus administered.

8. A pharmaceutical composition for intramammary administration to a non-human mammal, the pharmaceutical composition providing increased anti-inflammatory efficacy while not increasing immunosuppressive side effects in the non-human mammal, wherein:
the pharmaceutical composition comprises active agents and an inactive agent, wherein the active agents consist of cephapirin and 20 mg prednisolone; and the inactive agent comprises a pharmaceutically acceptable carrier; wherein the increased anti-inflammatory efficacy while not increasing immunosuppressive side effects may be determined by the non-human animal displaying a similar leukocyte count upon administration intramammarily thereto in comparison to the non-human mammal to which the pharmaceutical composition has not been thus administered.

9. The pharmaceutical composition of claim 7, wherein the cephalosporin is cephapirin present in an amount of 300 mg.

10. The pharmaceutical composition of claim 7, wherein the prednisolone and the cephalosporin are suspended in the pharmaceutically acceptable carrier, and wherein the pharmaceutically acceptable carrier comprises an oil and one or more pharmaceutically acceptable additives.

* * * * *